(12) United States Patent
Hamasaki et al.

(10) Patent No.: US 9,957,562 B2
(45) Date of Patent: May 1, 2018

(54) NUCLEIC ACID ANALYSIS DEVICE AND NUCLEIC ACID ANALYZER

(75) Inventors: Koshin Hamasaki, Hitachinaka (JP);
Toshiro Saito, Hitachinaka (JP);
Takayuki Obara, Ichihara (JP)

(73) Assignee: HITACHI HIGH-TECHNOLOGIES CORPORATION, Tokyo (JP)

( * ) Notice: Subject to any disclaimer, the term of this patent is extended or adjusted under 35 U.S.C. 154(b) by 688 days.

(21) Appl. No.: 14/002,125

(22) PCT Filed: Jan. 24, 2012

(86) PCT No.: PCT/JP2012/051388
§ 371 (c)(1),
(2), (4) Date: Aug. 29, 2013

(87) PCT Pub. No.: WO2012/124377
PCT Pub. Date: Sep. 20, 2012

(65) Prior Publication Data
US 2013/0338041 A1    Dec. 19, 2013

(30) Foreign Application Priority Data

Mar. 15, 2011  (JP) .................. 2011-057091

(51) Int. Cl.
*C12Q 1/68* (2006.01)
*G01N 21/64* (2006.01)
*C40B 40/06* (2006.01)

(52) U.S. Cl.
CPC ......... *C12Q 1/6876* (2013.01); *C12Q 1/6834* (2013.01); *C12Q 1/6874* (2013.01);
(Continued)

(58) Field of Classification Search
None
See application file for complete search history.

(56) References Cited

U.S. PATENT DOCUMENTS

2004/0248165 A1    12/2004 Takiguchi et al.
2005/0014151 A1    1/2005 Textor et al.
(Continued)

FOREIGN PATENT DOCUMENTS

JP    2004-294240 A    10/2004
JP    2006-250668 A    9/2006
(Continued)

OTHER PUBLICATIONS

Onoe et al., "Three-Dimensional Micro-Self-Assembly Using Hydrophobic Interaction Controlled by Self-Assembled Monolayers," J. Microelectromech. Syst. 2004, 13:603-611.*
(Continued)

*Primary Examiner* — Kaijiang Zhang
(74) *Attorney, Agent, or Firm* — Baker Botts L.L.P.

(57) ABSTRACT

In the conventional nucleic acid analysis devices and nucleic acid analyzers, there was no technique available for sequencing a single nucleic acid molecule easily and highly efficiently. The present invention enabled a highly efficient single molecule immobilization of nucleic acid with good reproductivity in a short time at a low price by providing small metallic bonding pads at predetermined positions on a support substrate, firmly fixing a hydrophobic linker on the bonding pads, and bonding on to the linker bulky microparticles onto which a single molecule of a nucleic acid sample fragment is immobilized. According to the present invention, in the nucleic acid analysis device which uses a nucleic acid analyzer, the nucleotide read length can be extended and many types of nucleic acid molecule to be analyzed can be analyzed at one time.

13 Claims, 5 Drawing Sheets

(52) U.S. Cl.
CPC ....... *G01N 21/648* (2013.01); *G01N 21/6452* (2013.01); *C40B 40/06* (2013.01); *G01N 2021/6439* (2013.01)

(56) References Cited

U.S. PATENT DOCUMENTS

2010/0009862 A1* 1/2010 Nakahara et al. .. G01N 21/6428
  506/9
2011/0281320 A1* 11/2011 Saito et al. .......... C12Q 1/6816
  435/176

FOREIGN PATENT DOCUMENTS

| JP | 2010-145272 A | 7/2010 | |
|---|---|---|---|
| JP | 2010-172271 A | 8/2010 | |
| WO | WO 2010087121 A1 * | 8/2010 | ........... C12Q 1/6816 |

OTHER PUBLICATIONS

John Eid et al., Real-Time DNA Sequencing from Single Polymerase Molecules, Science, Jan. 2, 2009, pp. 133-138, vol. 323.

* cited by examiner a b a b   A metallic thin film is formed by spattering.

c   Resist pattern formation d   Etching e   After peeling the resist, linear molecules selectively adsorbed to the bonding pad are incorporated.

f   Production of a non-specific adsorption prevention film

NUCLEIC ACID ANALYSIS DEVICE AND NUCLEIC ACID ANALYZER

TECHNICAL FIELD

The present invention relates to a nucleic acid analysis device and a nucleic acid analyzer comprising the device.

BACKGROUND ART

As a means for detecting a target substance such as DNA, proteins, or the like, commonly used is a method in which a target substance is labeled with fluorescence, irradiated with a predetermined excitation light such as laser, or the like, and the fluorescence thus emitted is detected. As an application of the method, a parallel sequencer, wherein DNA or RNA is immobilized on a substrate to determine the nucleotide sequence thereof, has been proposed. At present, commercially available parallel sequencers have dramatically improved the number of nucleotide read and the number of parallel per analysis by arranging a large number of DNA fragments to be read. Most of the parallel sequencers read a nucleotide sequence targeting clusters of copied DNA strands. However, the cluster formation not only requires time and the cost of a reagent but a phenomenon (dephasing) in which the sequence reaction loses the synchronicity between the DNA strands also occurs and hence limits the read length. Further, it is not suitable for quantitative analysis because the deviation is caused between the DNAs easy to be amplified and hard to be amplified. Thus, as a system for solving these drawbacks, a single molecule DNA sequencing method has been proposed. In this system, the nucleotide sequence for every single DNA molecule can be determined which thus eliminates the need for the purification and amplification of a sample DNA in cloning, PCR, or the like, that have been the problem in the conventional art, and hence faster genome analysis and gene diagnosis can be expected. One of such systems is SMRT technology of Pacific Biosciences Inc. (see Non-Patent Literature 1). In the SMART technology, a substrate in which a large number of several tens-nm holes called zero-mode waveguidances (ZMW) are aligned is produced and a single molecule of polymerase is placed in each of the holes. Nucleotides labeled with fluorescent dyes are incorporated therein and the fluorescence detection is carried out while the nucleotides are allowed to elongate to obtain the sequence information of each fragment. Such a technique wherein the detection is carried out while allowing the elongation with the incorporation of nucleotides is usually called Sequencing by synthesis. However, when the ZMW is used, the single molecule placement of a polymerase depends on the probability and consequently holes in which a single polymerase molecule is placed account for theoretically up to about 30% out of a large number of holes produced. In Sequencing by synthesis, a continuous nucleotide elongation reaction is detected and thus the field of vision to be detected cannot be moved until one cycle of elongation reaction is completed. Accordingly, to measure many samples at one time, it is desirable to immobilize samples as high density as possible, which is a factor to determine the final sequencing performance.

Various techniques have been reported for immobilizing on an analysis device a plurality of chemical substances such as nucleic acid, or the like, including DNA (see Patent Literatures 1 and 2).

CITATION LIST

Patent Literature

Patent Literature 1: U.S. Patent Serial No. 2005/0014151
Patent Literature 2: JP Patent Publication (Kokai) No. 2010-172271 A Non Patent Literature Non Patent Literature 1: Science 2009, Vol. 323. pp. 133-138

SUMMARY OF INVENTION

Technical Problem

In Patent Literature 1, a chemical substance having a selective binding property is adsorbed on a device consisting of a metal material and quartz to achieve a selective immobilization of a biological molecule and form a pattern on the device surface. However, in the immobilization technique described in Patent Literature 1, a plurality of small molecules having a size of several nm is immobilized on a substrate produced by a semiconductor process, and in such a technique the immobilization of a single nucleic acid molecule in a high probability is theoretically not possible. On the other hand, as described in Patent Literature 2, there is a technique in which single molecules of a nucleic acid probe are captured in advance onto bulky microparticles, which are arbitrary arrayed on metallic bonding pads to immobilize the molecules onto the pads. As an example thereof, a molecule having a functional group selectively adsorbed by the bonding pad is used as the linker molecule for connecting the microparticle and the bonding pad, and biotin is added within the molecule. The microparticle is, on the other hand, conjugated with avidin to achieve the immobilization by the avidin-biotin binding. This technique is capable of immobilizing the microparticles one by one on the bonding pad and enables the immobilization of a single nucleic acid molecule. However, the drawback posed in this technique is that when biotin is incorporated in a small bonding pattern via a functional group, some of the bonding pads had a low density of incorporated biotin. This is presumably caused by a low amount of biotin incorporated per binding molecule and the inconsistent synthesis reaction of biotinylated binding molecules. It is difficult, not only limited to this example of biotin, to uniformly incorporate binding molecules in an sufficient amount for immobilizing microparticles on a small pattern, which is the portion formed on an analysis device for immobilizing a nucleic acid.

An object of the present invention is to provide, to solve the problems posed by the conventional art, a method for arraying single molecules of a nucleic acid probe in a high density at predetermined immobilization positions easily and highly efficiently by using microparticles and a hydrophobic linker.

Solution to Problem

The present inventors conducted extensive studies on a method which solves the problems posed in the conventional technique for binding a chemical substance to an analysis device, immobilizes single molecules of nucleic acid on an analysis device in a high probability, and uniformly on the portions at which the nucleic acid is immobilized, that is, immobilizes single molecules substantially throughout the entire portion. The present inventors have come up to an idea of using a hydrophobic interaction as a method for binding onto a substrate microparticles onto which a single probe molecule is immobilized in place of the specific binding between the specific molecules as in the method described in the above Patent Literature 2. It was difficult to predict that microparticles can be firmly bound on a substrate by the hydrophobic interaction, but the present inventors surprisingly found that the immobilization method, which employs the hydrophobic interaction using an SAM film (Self-Assembled Monolayer) of hydrophobic alkyl chain and hydrophobic nanosize microparticles, is suitable for immobilizing nanosize microparticles, and allowing the binding in a high density to a small pattern portion formed on an analysis device at which a nucleic acid is immobilized. As a result, the present inventors accomplished the single molecule immobilization method using microparticles, which can be carried out in a short time at a low cost with good consistency. According to the present invention, small metallic bonding pads are provided at predetermined positions on a support substrate, a hydrophobic linker having an alkyl chain as the main component is immobilized on the metallic bonding pads, whereby microparticles can be arrayed in a high efficiency on the linker.

The present specification encompasses the contents described in the specification and/or drawings of Japanese Patent Application No. 2011-057091, which is the basis of priority of the present application.

Advantageous Effects of Invention

The nucleic acid analysis device of the present invention has a flat support substrate having metallic bonding pads formed regularly, each of which has a single molecule of a probe immobilized on a microparticle, which is immobilized using a hydrophobic interaction on the pads, wherein single molecules of the probe are immobilized uniformly on the bonding pads in a high probability. More specifically, according to the present invention, a nucleic acid analysis device in which a probe molecule of small molecule is immobilized at predetermined positions in a high efficiency can be provided at a low cost, and a nucleic acid analysis such as determining a DNA sequence, or the like, can be carried out in a high throughput using the nucleic acid analysis device and the nucleic acid analyzer comprising the same of the present invention.

BRIEF DESCRIPTION OF DRAWINGS

FIG. 1a shows the state in which a microparticle is immobilized on a bonding pad, and FIG. 1b shows the state in which the bonding pads on which microparticles are immobilized are regularly aligned on the substrate.

FIG. 2a shows the state in which a microparticle is immobilized on a bonding pad, and FIG. 2b shows the state in which the bonding pads on which microparticles are immobilized are regularly aligned on the substrate.

FIG. 4A shows a method (steps a to e) in which a metal thin film is formed on a flat support substrate, a pattern is then formed by resist and a flat covering film is subsequently formed, and FIG. 4B shows a method (steps a to e) in which a flat covering film is formed on a flat support substrate and a pattern is formed by resist.

DESCRIPTION OF EMBODIMENTS

Figure 1:
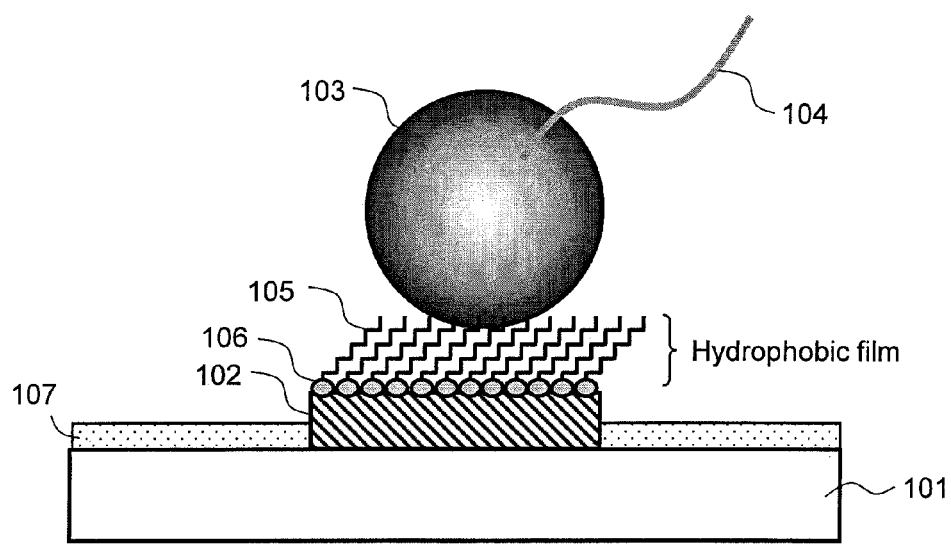
FIGS. 1a and 1b are drawings showing the structure of a nucleic acid analysis device of Example 1 wherein microparticles onto which a probe molecule is captured are arrayed.
Figure 1:
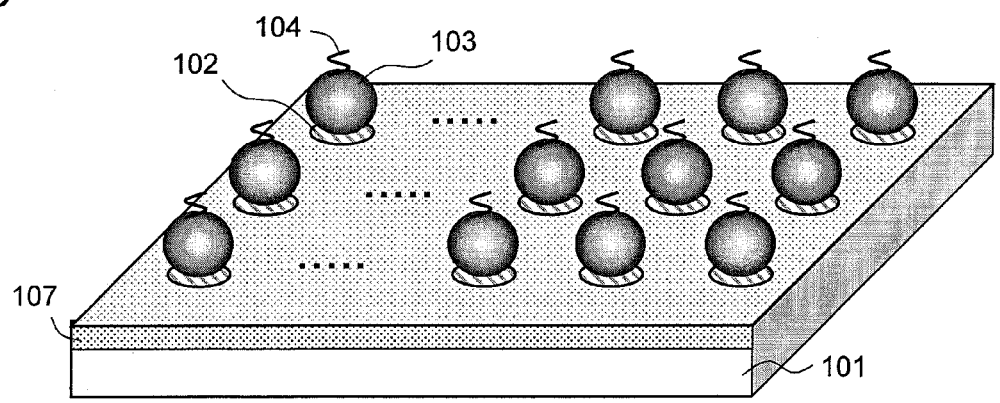

The present example discloses a nucleic acid analysis device comprising a support substrate and microparticles having a probe molecule capable of capturing a nucleic acid to be detected, wherein each of the microparticles is immobilized separately from each other on the support substrate, the nucleic acid analysis device comprising hydrophobically treated bonding pads at positions at which the microparticles are immobilized on the substrate, wherein the microparticles are immobilized by a hydrophobic interaction on the bonding pads.

Further, the present example discloses a nucleic acid analyzer for obtaining nucleotide sequence information of a nucleic acid sample, the analyzer comprising: a means for supplying a nucleotide having a fluorescent dye, and a nucleic acid sample to the nucleic acid analysis device produced by selecting only the microparticles having a single probe molecule and regularly immobilizing the selected microparticles on the bonding pad on the support substrate; a means for irradiating the nucleic acid analysis device with evanescent light, and a luminescence detector for measuring the fluorescence of the fluorescent dye incorporated into a nucleic acid chain through the nucleic acid elongation reaction induced by the coexistence of the nucleotide, the nucleic acid polymerase, and the nucleic acid sample on the nucleic acid analysis device.

Furthermore, the present example discloses a nucleic acid analysis device comprising bonding pads at immobilization positions of the microparticles on the support substrate, wherein the microparticles and the bonding pads are bound by the hydrophobic interaction of alkyl chains, the diameter of the bonding pads are ⅕ to 5 times the size of the microparticles, and the support substrate surface has a thin film layer made of an organic polymer for preventing non-specific adsorption.

Still furthermore, the present example discloses that a single probe molecule is immobilized on a single microparticle.

Further, the present example discloses that the bonding pads are made of a material selected from the group consisting of gold, titanium, nickel and aluminum.

Furthermore, the present example discloses that the organic polymer for preventing the non-specific adsorption of the microparticle is made of a material selected from polyethylene glycol (PEG), polyacrylamide, polymethoxy ethyl acrylate, 3-glycidoxypropylmethoxysilane (GOPS), and the like.

Still furthermore, the present example discloses an evanescent field as a means for irradiating the above nucleic acid analysis device with light.

Hereinbelow, the above and other novel features and effects of the present invention are described with reference to the drawings. A specific embodiment is described in detail for thorough understanding of the present invention, but the present invention is not limited to the content described herein.

The structure of a device of the present example is described with reference to FIG. 1.

FIG. 1a shows the state in which a bonding pad 102 is formed on a flat support substrate 101, and a microparticle 103 on which a probe molecule 104 is immobilized is bound on the bonding pad by a hydrophobic interaction via a hydrophobic film formed of linear molecules 105 having an end functional group 106, and FIG. 1b shows the state in which a plurality of the microparticles 103 on which a probe molecule 104 is immobilized is regularly immobilized on the bonding pads 102 on the flat support substrate 101.

The bonding pads 102 on the flat support substrate 101 are formed regularly in a large number, and are formed, for example, in a grid pattern as shown in FIG.1b. The bonding pad 102 and the microparticle 103 are chemically bound via the linear molecule 105. A thin film 107 for preventing a non-specific adsorption is formed in the region other than the region on which the bonding pads 102 are formed on the flat support substrate 101. The thin film is called a non-specific adsorption prevention film. The end functional group 106 of the linear molecule 105 is preferably bound to the bonding pad 102 by the hydrophobic interaction established by an alkyl chain. The functional group 106 preferably has the weak interaction with the flat support substrate 101 or the thin film of non-specific adsorption prevention 107, but has the firm binding to the bonding pad 102, due to which the microparticle on which the probe molecule 104 is immobilized is immobilized only on the bonding pad 102. More specifically, the microparticle 103 can be selectively bound to the bonding pad 102. In the present invention, the binding of the microparticles 103 on the flat support substrate 101 in a regular pattern is called the formation of pattern (patterning), and the selective binding only to the bonding pad 102 region on the flat support substrate 101 is termed as having pattern selectivity.

From this perspective, the flat support substrate 101, the bonding pad 102 and the functional group 106 of the linear molecule 105 may be selected in the combination so that the firm binding is established between the bonding pad 102 and the functional group 106 but the firm binding is not established between the flat support substrate 101 and the functional group 106.

For the flat support substrate 101, a quartz glass, sapphire, a silicon substrate, or the like, can be used. The size of the flat support substrate 101 can be suitably designed in accordance with the purpose of use, but, for example, tetragonal ones can be used. In the present invention, the flat support substrate is sometimes simply referred to as a substrate.

Further, the bonding pad 102 can be composed of a metallic material selected from the group consisting of gold (Au), titanium (Ti), nickel (Ni) and aluminum (Al). The thin metallic film described above may further be formed on the metallic pad. The size of the bonding pad 102 depends on the purpose of use and the size of flat support substrate, but, for example, circular ones can be used. Also, the shape is not limited, and tetragons such as square, rectangles, and other irregular shapes may be used.

The functional group 106 of the linear molecule 105 must be selected in consideration of the combination of the flat support substrate 101 and the bonding pad 102 as described above, and, for example, a sulfhydryl group (thiol group), an amino group, a carboxyl group, a phosphoric acid group, an aldehyde group, or the like, may be used. The hydroxyl group of sugar may also be used. Of these, the combination may be selected so that the firm binding is established between the functional group 106 and the bonding pad 102, the firm binding is not established between the functional group 106 and the flat support substrate 101, or no binding is established. Hereinbelow, metallic materials to which a sulfhydryl group, an amino group, a carboxyl group, a phosphoric acid group, an aldehyde group or the hydroxyl group of sugar is easily adsorbed.

| | |
|---|---|
| Sulfhydryl group | Au, Ni |
| Amino group | Ti, Ni |
| Carboxyl group | Ti |
| Phosphoric acid group | Ti, Al |
| Aldehyde group | Ti, Ni |
| Hydroxyl group of sugar | Ti |

Also, of the above functional groups, the amino group, carboxyl group and aldehyde group have a low selectivity with quartz and hardly bind to quartz.

Accordingly, the preferable combinations are, for example, a quartz glass used as the flat support substrate 101, an amino group used as the functional group 106 and titanium or nickel used as the bonding pad 102, a quartz glass used as the flat support substrate 101, a carboxyl group used as the functional group 106 and titanium used as the bonding pad 102, or a quartz glass used as the flat support substrate 101, an aldehyde group used as the functional group 106 and titanium or nickel used as the bonding pad 102. However, the combination is not limited thereto, and any combinations of the above materials can be used. For example, a quartz glass used as the flat support substrate 101, the glycoside group of sugar used as the functional group 106 and titanium used as the bonding pad 102 can be used in combination. In the case of the combination of glycoside group of sugar and titanium, the binding of the glycoside group of sugar and titanium can be controlled by changing the pH, or the like. Consequently, after using the nucleic acid analysis device, for example, the pH is changed, the linear molecule 105 is removed from the bonding pad 102 to reuse the flat support substrate 101 including the bonding pad 102. Also, as to be described later, the non-specific adsorption prevention film 107 is formed on the region other than the region on which the bonding pads 102 are formed on the flat support substrate 101. The functional groups other than the glycoside group of sugar easily bind to the non-specific adsorption prevention film 107. Accordingly, when a functional group other than the glycoside group of sugar is used as the functional group 106, the non-specific adsorption prevention film must be formed after the functional group 106 of the linear molecule 105 is allowed to bind to the bonding pad 102. The glycoside group of sugar, on the other hand, is not likely to bind, or does not bind, to the non-specific adsorption prevention film 107. For this reason, when the glycoside group of sugar is used as the functional group, the order of the immobilization of the linear molecule on the bonding pad 102 and the formation of the non-specific adsorption prevention film is irrelevant.

For the linear molecule 105, an amphipathic molecule having the above functional group 106 at the end of a hydrophobic compound can be used. The linear molecule 105 has a hydrophobic moiety, due to which the interaction occurs between the linear molecule 105 and the microparticle 103 and serves to connect the microparticle 103 and the bonding pad 102. More specifically, the linear molecule 105 functions as a hydrophobic linker to bind the bonding pad 102 and the microparticle 103. Examples of the hydrophobic moiety of the linear molecule 105 include an alkyl chain. The alkyl chain is preferably a straight chain. The length of alkyl chain is not limited but, in terms of the carbon number, preferably 3 to 20, and more preferably 8 to 12.

Examples of the linear molecule 105 having the functional group 106 satisfying the above include alkylphosphate, alkyl sulfonic acid, alkyl glycoside (sugar alkyl), and the like. Specific examples include propylphosphoric acid, butylphosphoric acid, pentyl phosphoric acid, hexyl phosphoric acid, heptyl phosphoric acid, octylphosphoric acid, nonylphosphoric acid, decylphosphoric acid, undecylphosphoric acid, dodecylphosphoric acid, tridecylphosphoric acid, tetradecylphosphoric acid, pentadecylphosphoric acid, hexadecylphosphoric acid, heptadecylphosphoric acid, octadecylphosphoric acid, nonadecylphosphoric acid, eicosyl phosphoric acid; propylsulfonic acid, butylsulfonic acid, pentylsulfonic acid, hexylsulfonic acid, heptylsulfonic acid, octylsulfonic acid, nonylsulfonic acid, decylsulfonic acid, undecylsulfonic acid, dodecylsulfonic acid, tridecylsulfonic acid, tetradecylsulfonic acid, pentadecylsulfonic acid, hexadecylsulfonic acid, heptadecylsulfonic acid, octadecylsulfonic acid, nonadecylsulfonic acid, eicosylsulfonic acid; propyl glycoside, butyl glycoside, pentyl glycoside, hexyl glycoside, heptyl glycoside, octyl glycoside, nonyl glycoside, decyl glycoside, undecyl glycoside, dodecyl glycoside, tridecyl glycoside, tetradecyl glycoside, pentadecyl glycoside, hexadecyl glycoside, heptadecyl glycoside, octadecyl glycoside, nonadecyl glycoside, eicosyl glycoside, and the like. The alkyl chain forms a high density self-assembled monolayer (SAM film) and imparts the hydrophobic property on the bonding pad. In the present invention, the SAM film formed by the alkyl chain is also called a hydrophobic film. The hydrophobic property used herein refers to a low wettability to water and has a contact angle of more than a certain degree. More specifically, when water contacts the SAM film formed by an alkyl chain, the contact angle of a water drop to the SAM film is more than a certain degree. Typically, the hydrophobic property refers to the case in which a contact angle is 90° C. or more. However, in the present invention, when a contact angle is 50° or more, the pattern selectivity becomes larger and it is verified that the sufficient immobilization force between the microparticle 103 and the bonding pads 102 is further attained. The hydrophobic interaction is the phenomenon in which hydrophobic molecules clump up together rather than distributing itself in water, and thus in the present invention which uses water as the main component of the reaction solution, the hydrophobicity even lower than that based on the typical definition is considered to be sufficiently functional from the perspective of imparting the firm binding between the microparticle 103 and the bonding pad 102. For the above reason, the alkyl chain contained in the linear molecule 105 may have the hydrophobic property having a contact angle of 50° or more. The linear molecule may contain other functional groups or may have a structural modification as long as a contact angle is 50° or more.

Further, the thin film for preventing the non-specific adsorption (non-specific adsorption prevention film) 107 is formed at a contact angle of 50° or more on the region other than the region on which the bonding pads 102 are formed on the flat support substrate 101. The thin film 107 is preferably made of an organic polymer material which prevents the non-specific adsorption of other compounds to the region other than the region on which the bonding pads 102 for the microparticles 103 are formed on the flat support substrate 101. Examples of the organic polymer material usable include polyethylene glycol (PEG), poly-L-lysine PEG (pLL-PEG), polyacrylamide, 3-glycidoxypropylmethoxysilane (GOPS), and the like. The method for forming the non-specific adsorption prevention film 107 is not limited and a known method is employed, but, for example, the non-specific adsorption prevention film 107 can be formed by the silane coupling using a PEG silane agent, or the like. The non-specific adsorption prevention film 107 is not formed on the bonding pad 102.

The microparticle 103 hydrophobically interacts with the alkyl chain of the linear molecule 105 and is immobilized on the bonding pad 102 via the linear molecule 105. Thus, the material itself composing the microparticle 103 must be hydrophobic, or the microparticle 103 must be hydrophobically treated by being conjugated with a hydrophobic substance such as a hydrophobic protein, or the like. Examples of such a microparticle 103 include organic polymer microparticles such as resin microparticles including polystyrene, polypropylene, and the like, semiconductor microparticles such as quantum dots (semiconductor nano particles) made of a semiconductor material including cadmium selenide (CdSe), zinc sulfide (ZnS), cadmium sulfide (CdS), zinc selenide (ZnSe), zinc oxide (ZnO), and the like, metallic microparticles such as gold microparticles, and the like, polymer microparticles such as silica microparticles, and the like. These microparticles are used without further treatment when made of a hydrophobic material, whereas the microparticles, when otherwise, may be conjugated with a hydrophobic conjugation substance. The term conjugation used herein means to bind a conjugation substance to the microparticle surface, more specifically, to cover a part of or throughout the entire microparticle surface with a conjugation substance. Proteins are preferably used to be the conjugation substances, and avidin which is also usable as the probe of microparticle is preferably used to be the conjugation protein. The average particle diameter of the microparticle 103 is preferably 10 nm to 1 μm, more preferably 40 nm.

A single microparticle 103 is immobilized on a single bonding pad 102. In other words, the microparticle 103 is spatially immobilized on the flat support substrate 101 so as not contact with each other.

For this reason, the diameter of the bonding pad is ⅕ to 5 times the diameter of the microparticle, and preferably less than or equal to the diameter of the microparticle.

The probe molecule is not limited, but a single strand nucleic acid molecule of DNA or RNA capable of capturing the nucleic acid to be detected or analyzed in the present invention may be used. The nucleic acid to be detected or analyzed by the probe molecule is captured by the hybridization of the probe molecule and the nucleic acid to be detected or analyzed. The size of probe molecule is not also limited, and the probe molecule may be an adaptor molecule such as adaptor DNA, or the like, and in such a case the nucleic acid molecule to be analyzed is immobilized to the microparticle by binding a nucleic acid fragment complementarily hybridizable to the adaptor DNA immobilized on the microparticle to the nucleic acid to be analyzed.

The nucleic acid analysis device shown in FIG. 1 consists of the above flat support substrate 101, the bonding pad 102, the microparticle 103 on which the probe molecule 104 is immobilized, the linear molecule 105 and the non-specific adsorption film 107.

The formation of the bonding pad 102 on the flat support substrate 101 is carried out by using a known thin film process used for forming a semiconductor.

The binding of the linear molecule 105 to the bonding pad 102 is carried out by allowing a solution of the linear molecule 105 to contact the bonding pad 102, and, for example, the flat support substrate 101 on which the bonding pads 102 are formed may be immersed in the solution of the linear molecule 105 for a predetermined period of time at a predetermined temperature.

After binding the linear molecule 105 to the bonding pad 102, the non-specific adsorption prevention film 107 is formed on the region other than the region on which the bonding pads 102 are formed on the flat support substrate 101. The formation of the non-specific adsorption prevention film 107 is carried out by silane coupling using as the silane coupling agent a silane derivative of an organic polymer which is to be a material for the non-specific adsorption prevention film 107 and forming a thin silane film of the organic polymer. The silane film is not produced on the metallic bonding pad 102, or produced in a very weak force. The silane film bound on the metallic bonding pad can be removed by, for example, washing using a surfactant such as SDS, or the like.

The order of binding the linear molecule 105 for bonding to the bonding pad 102 and the formation of the non-specific adsorption prevention film 107 is not limited, but the order may be determined in consideration of the binding properties of the functional group 106 of the linear molecule 105 and the organic polymer such as PEG, or the like, to be used for forming the non-specific adsorption prevention film 107. For example, when the functional group of the linear molecule 105 is other than the hydroxyl group of sugar, e.g., when the linear molecule 105 is alkylphosphate, it easily binds to an organic polymer such as PEG, or the like, and hence it is preferable to form the non-specific adsorption prevention film 107 after the linear molecule 105 is bound to the bonding pad 102. On the other hand, when the functional group of the linear molecule 105 is the hydroxyl group of sugar, the linear molecule 105 can be bound to the bonding pad 102 after the non-specific adsorption prevention film 107 is formed since such a linear molecule does not easily bind to an organic polymer such as PEG, or the like.

The immobilization of the probe molecule 104 to the microparticle 103 is carried out so that a single probe molecule is immobilized to a single microparticle. The method for immobilizing a single probe molecule to a single microparticle is described in Example 1. The method for binding the probe molecule 104 to the microparticle 103 is not limited and may be chemical or physical binding, but, for example, avidin or streptavidin is bound to the microparticle 103, while biotin is bound to the probe molecule 104, thereby achieving the binding using the avidin-biotin binding. Alternatively, the binding is attained by the adsorption.

The microparticle 103 on which the probe molecule 104 is immobilized is made contact with the flat support substrate 101, on which the bonding pads 102 are formed and the non-specific adsorption prevention film 107 is formed. Since the microparticle 103 has the hydrophobic surface or is conjugated with a hydrophobic conjugation substance, the hydrophobic interaction occurs between the hydrophobic linear molecule 105 bound on the bonding pad 102 and the microparticle 103, whereby the microparticle 103 is immobilized on the bonding pad 102.

Thus, the flat support substrate 101 to which the probe molecule 104 is bound can be produced. The presence of the probe molecule 104 on the flat support substrate 101 can be confirmed using, for example, a laser microscope.

EXAMPLE 1

Hereinbelow, an example is shown in which the microparticle 103 on which the probe molecule 104 is immobilized is actually immobilized on the nucleic acid analysis device. In this example, a nucleic acid analysis device was produced for use in which titanium bonding pads having a thickness of 10 nm and a diameter of 60 nm are arrayed in a grid pattern with a 1 μm interval on a quartz glass substrate having a thickness of 0.7 mm.

For the method for forming the bonding pad 102 on the quartz glass substrate, the thin film process which has already been used practically in the semiconductors was applied. More specifically, after forming a titanium thin film by the vapor deposition-sputtering through a mask, and the vapor deposition-sputtering, a resist pattern was formed by lithography using EB, and the bonding pad was produced by dry and wet etchings. The interval among the bonding pads 102 may be arbitrary set, but is preferably 500 nm or more when an optical measurement is carried out as the detective means in consideration of the diffraction limit of optical detection. The formation method of the bonding pad is described in detail in Example 3.

The linear molecule 105 for immobilizing the microparticle was reacted and bound on the bonding pad 102 of the nucleic acid analysis device. In the present example, dodecylphosphoric acid, which is alkylphosphate, was used as the linear molecule 105. A solution in which a powder of dodecylphosphoric acid was dispersed in ultra pure water in a concentration of 0.3 mM was prepared, and the nucleic acid analysis device on which the bonding pads 102 produced by the above method were formed was immersed in the solution and treated at 90° C. for an hour or more. When treating using dodecylphospholic acid in a concentration of 0.3 mM, the solubility of dodecylphospholic acid is enhanced by adding the equimolar amount of ammonia. Alternatively, ammonium dodecyl phosphate may be directly dissolved in water. At this time, the linear molecule 105 did not bind to the region other than the bonding pads 102 on the quartz glass substrate due to the binding selectivity between the functional group 106 of the linear molecule 105 and the bonding pad 102.

Next, the non-specific adsorption prevention film 107 was formed on the quartz glass surface of the nucleic acid analysis device using a PEG silane agent. Using 2-methoxypolyethyleneoxypropyltrimethoxysilane (produced by Gelest, Inc., Mw: 2,000) as the PEG silane agent, an SAM film was produced to be the non-specific adsorption prevention film. In the production method, the PEG silane agent was dissolved in a toluene solvent so as to give 3 mM and triethylamine was added as a catalyst to give the final concentration of 1%. The nucleic acid analysis device was immersed in the mixed solution and reacted for 30 minutes at 60° C. The nucleic acid analysis device was washed using toluene and ethanol after taken out from the mixed solution and baked at 90° C. for 10 minutes using an electric furnace. The film thickness of silane film on the substrate was measured using a spectroscopic ellipsometer, and the result found that the silane film had a film thickness of 20 Å. It is also verified that the PEG silane film was not produced on the bonding pad to which dodecylphospholic acid was bound.

Subsequently, the microparticle on which a single molecule of the nucleic acid probe was immobilized was reacted to the nucleic acid analysis device treated in the above at room temperature for 15 minutes or more. A polystyrene NeutrAvidin-conjugated bead (FluoSpheres (registered trademark) F8773 Invitrogen) having a diameter of 40 nm was used as the microparticle. Biotinylated DNA was used as the probe molecule for capturing a nucleic acid.

A method for binding a single probe molecule to a single microparticle is described below. In the present example, a nucleic acid sample fragment, in which the end of polynucleotide composed of 50 to 100 bases was biotinylated and the 5'-end was fluorescence-labeled with Cy3, was used as the probe molecule. When the number of microparticle is increased 10 times the number of probe molecule for the reaction, the probe molecules are not captured in about 90% of the microparticles and a single probe molecule is captured by the avidin-biotin binding in about 9% of the microparticles. This result exactly matches the prediction results of when the Poisson distribution is assumed. Accordingly, when collecting only the microparticles which captured the probe molecule, 90% or more of the collected microparticles are those which captured only a single probe molecule. In this condition, the microparticles to which a single probe molecule is bound can be obtained in much higher purity using molecular weight separation, magnetic microparticle collection, electrophoresis separation using an electrical charge difference, or the like. The probe molecule 104 immobilized on the substrate 101 was confirmed using a total internal reflection laser microscope. After the immobilization reaction of the microparticles, YAG laser (532 nm) is incident to the substrate back side under the condition of total reflection while the substrate top is filled with water, and the projected fluorescence was condensed from the substrate top side through an objective lens for CCD camera observation. A single molecule of Cy3 can be confirmed when Cy3 is excited with a laser, caused to light up and quenches in a single stage. When Cy3 is more than 2 molecules, a multistage quenching occurs. The single molecule immobilization rate was calculated by this method and the results revealed that a single molecule of the probe molecule 104 was immobilized on 70% or more of the bonding pads. Further, when 500 pieces of the bonding pads of the nucleic acid analysis device were observed at random using a scanning electron microscope (SEM), the microparticles were revealed to have been immobilized in an immobilization rate of about 90%.

In accordance with the method shown in Example 1 of Patent Literature 2, when using PVPA (polyvinyl phosphonic acid) in which 30 molecules of biotin were incorporated in a single molecule, microparticles conjugated with streptavidin in a 500 nM density was reacted therewith for 2 hours to immobilize the microparticles on the substrate by the streptavidin-biotin binding, the microparticle has an immobilization density on the substrate of 30 to 50 pieces/$\mu m^2$. In contrast with this method, when microparticles in the same density were reacted using dodecylphospholic acid for 2 hours to immobilize the microparticles on a substrate by the hydrophobic interaction in accordance with the method of the present example, the microparticle had an immobilization density of 80 to 100 pieces/$\mu m^2$. The immobilization amount of the microparticle was substantially saturated in the 2 hour-reaction. Consequently, the method wherein dodecylphospholic acid was used according to the present example has a higher density as the bonding molecule on the substrate. Further, it was revealed that when dodecylphospholic acid was used, the immobilization reaction of the microparticles reached 60 to 80 pieces/$\mu m^2$ in 10 minutes and substantially saturated in 30 minutes from the start. The reaction rate is about 5 times the rate in the case where the biotin-incorporated PVPA is used. This is presumably due to the influence of the electrical charge difference at the metal portion on which the linear molecule 105 is attached. Both of the linear molecules use a phosphoric acid group as the functional group, and thus the bonding pads are negatively charged. For this reason, the electric repulsion is caused against the microparticles which are also similarly negatively charged. However, the dodecyl phosphoric acid has the alkyl chain moiety whose film thickness reaches 2 to 3 nm and hence the negative electric charge at the outermost surface is reduced and the above electric repulsion is also decreased, whereby the immobilization reaction rate when the microparticles are bound to the bonding pads is thought to be enhanced. As described above, the present example demonstrated the result that it is more advantageous to use dodecyl phosphoric acid as the linker for binding the microparticles to the substrate, that is, to bind the microparticles to the substrate using the hydrophobic interaction. Further, the dodecyl phosphoric acid preparation which only requires the dissolution in water can be carried out in an extremely short time at an inexpensive price and furthermore has advantageously good reproductivity, and thus the method according to the present invention in which the microparticles are bound to the substrate using the hydrophobic interaction is very effective.

There are some systems conceivable for the method for detecting information on a nucleic acid sample from the nucleic acid analysis device of the present example, but the method which uses the fluorometric detection is preferable in light of sensitivity and convenience. First, a nucleic acid sample is supplied to the nucleic acid analysis device and the probe molecule 104 is allowed to capture the nucleic acid sample. Next, a nucleotide having a fluorescent dye is supplied, and when the probe molecule 104 is a DNA probe, a nucleic acid polymerase is supplied. The fluorescent dye incorporated into the nucleic acid chain during the nucleic acid elongation reaction occurred on the device is subjected to the fluorescence measurement. In this case, the so-called sequential elongation reaction system, in which one kind of nucleotide is supplied, unreacted nucleotides are washed and fluorescence imaged, a different kind of nucleotide is supplied and the same procedure is repeated thereafter, is easily carried out. The fluorescent dye is quenched after the fluorescence observation or the nucleotide in which the fluorescent dye is attached to the phosphoric acid moiety is used to cause the sequential reaction, whereby the nucleotide sequence information of the nucleic acid sample can be obtained. Alternatively, the so-called real time reaction system can also be carried out by supplying 4 kinds of nucleotide having different fluorescent dyes respectively without washing to cause a sequential nucleic acid elongation reaction and continuously carrying out the fluorescence observation. In this case, when the nucleotide in which the fluorescent dye is attached to the phosphoric acid moiety is used, the phosphoric acid moiety is cut off after the elongation reaction and thus the fluorescence measurement is continuously carried out without quenching to obtain the nucleotide sequence information of the nucleic acid sample.

EXAMPLE 2

In Example 2, an example is shown wherein octyl glucoside, which is an alkyl glycoside non-ionic surfactant, is used as the linear molecule 105 and a semiconductor quantum dot is used as the microparticle 103. In this example, the nucleic acid analysis device had the same components as in Example 1, provided that the flat support substrate 101 had the titanium bonding pad 102 having a diameter of 20 nm. Examples of the advantage of using octyl glucoside include that the linear molecule 105 for bonding the microparticles can be reacted even after the production of the non-specific adsorption prevention film 107 and the linear molecule 105 is removable by changing the pH, or the like. Alkylphosphate comparatively easily adheres to PEG and it is hence required to treat the bonding pad 102 with alkylphosphate before forming the non-specific adsorption prevention film 107 for binding alkylphosphate to the bonding pad 102. On the other hand, when alkyl glycoside such as octyl glucoside is used, alkyl glucoside is bound on the bonding pad 102 after forming the non-specific adsorption prevention film 107 by producing a PEG silane film since alkyl glucoside is hardly adsorbed to the non-specific adsorption prevention film 107, whereby the hydrophobic patterning is enabled. Consequently, when alkyl glucoside is used as the linear molecule 105, alkyl glucoside is removable from the substrate after the nucleic acid analysis device is used, thereby being beneficial for repeatedly using the nucleic acid analysis device.

In the present example, using 2-methoxypolyethyleneoxypropyltrimethoxysilane (produced by Gelest, Inc., Mw: 2,000) as the PEG silane agent as in Example 1, a self-assembled monolayer (SAM film) was produced in the same manner as in Example 1 on the nucleic acid analysis device as the non-specific adsorption prevention film 107. The PEG silane film is also formed on the metallic bonding pads, however, since the binding force thereof is extremely weaker to a metal than the bonding to a quartz glass, only the PEG silane film on the bonding pads is selectively peeled off by washing with a 0.1% SDS solution. Subsequently, the nucleic acid analysis device was immersed in a 1% octyl glucoside aqueous solution and reacted at 60° C. for 30 minutes. The device was washed with ultra pure water and baked at 90° C. for 10 minutes using an electric furnace. The microparticle was then reacted to the above treated nucleic acid analysis device at room temperature for 15 minutes or more. The microparticle used was a quantum dot (Qdot (registered trademark) 705 StreptAvidin Conjugated, Invitrogen) having a CdSe core diameter of 15 nm and conjugated with streptavidin. A polystyrene NeutrAvidin-conjugated bead (FluoSpheres (registered trademark) F8773, Invitrogen) having a diameter of 40 nm can also be used. Further, when the nucleic acid analysis device was observed using a scanning electron microscope (SEM), it was revealed that the microparticles were immobilized in an immobilization rate of about 90% or more. An example of the advantage for using the quantum dot as the microparticle is that the FRET effect can be used. In other words, using the quantum dot as the energy donor by light irradiation, the fluorescent dye labeling the nucleic acid molecule to be detected captured when analyzing the nucleic acid is actuated as an acceptor for the above energy, thereby enabling the detection by the fluorescence of the detection target molecule. Since the energy transfer is the phenomenon which only occurs in the vicinity of about less than or equal to 10 nm, it is effective in the case where the nucleic acid molecule to be detected is labeled with the same fluorescent dye and a specific molecule is detected in a high concentration of the sample solution. In this instance, the source of excitation light only needs to excite the semiconductor microparticles, and the light source may be only one kind, hence preferable.

Figure 2:
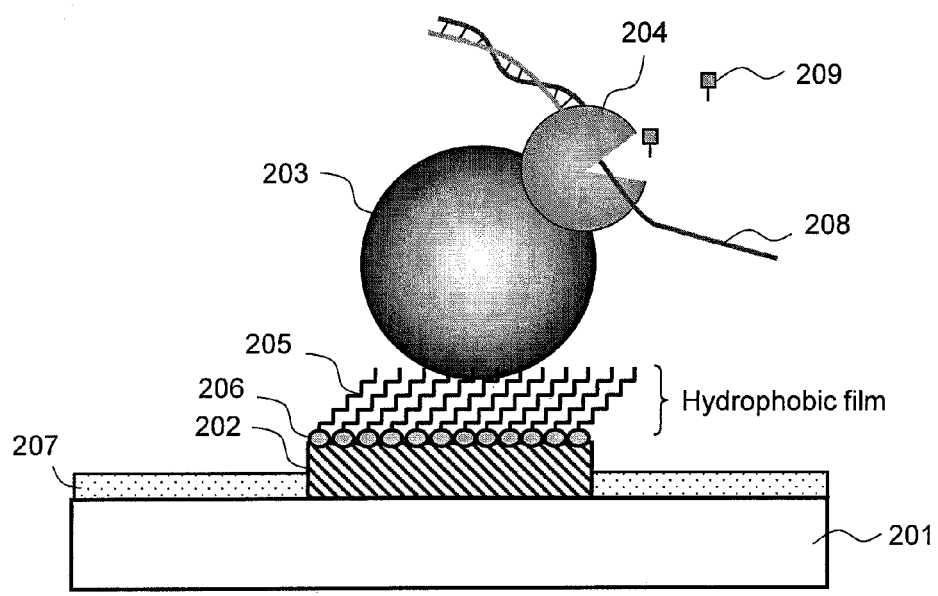
FIGS. 2a and 2b are drawings showing the structure of a nucleic acid analysis device of Example 2 wherein microparticles onto which a nucleic acid polymerase is captured are arrayed.
Figure 2:
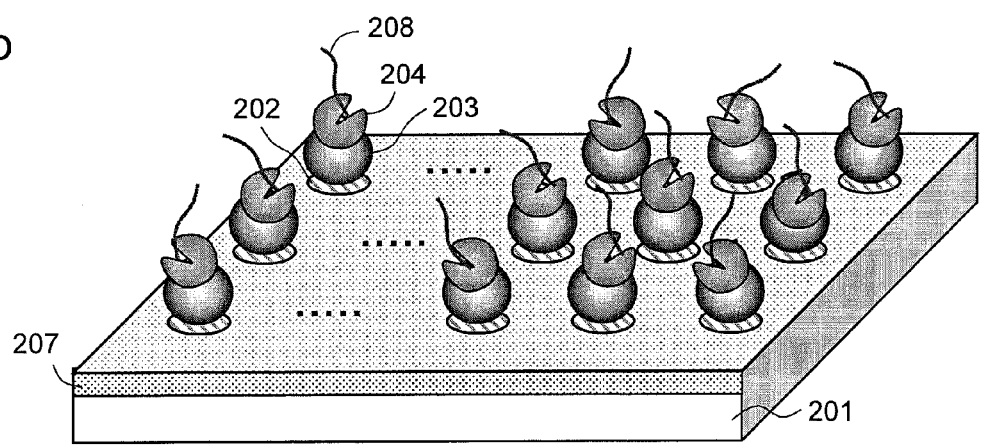

Also, as in FIG. 2, a method in which a single molecule of DNA polymerase 204, which is a nucleic acid polymerase, is immobilized on a microparticle 203 (enzyme immobilization method) can be used. FIG. 2a shows the state in which a bonding pad 202 is formed on a flat support substrate 201, and a microparticle 203 on which the DNA polymerase 204 is immobilized is bound on the bonding pad by a hydrophobic interaction via a hydrophobic film formed from linear molecules 205 having an end functional group 206, and FIG. 2b shows the state in which the microparticles 203 on which the DNA polymerase 204 is immobilized are regularly formed on the bonding pads 202 on the flat support substrate 201. In this method, as the one-to-one immobilization of the nucleic acid molecule and microparticle described in Example 1, a microparticle attached with a single molecule of DNA polymerase is produced by the probability reaction. The microparticle surface is conjugated with an epoxy group, a tosyl group, an amino group, a carbonyl group to immobilize a DNA polymerase thereon. It is particularly preferable to react the microparticle with an epoxy group which does not deactivate the DNA polymerase and enables a moderate binding reaction to proceed. Next, the produced enzyme-attached microparticles are immobilized on the bonding pads 202. Subsequently, when fluorescence-labeled 4 kinds of bases (A, T, C, G) 209 are incorporated in the reaction solution, the DNA polymerase captures a nucleic acid molecule 208 to be a template and keeps adding nucleotides one after another complementary to the template, thereby proceeding the DNA elongation reaction. During this process, the microparticles are irradiated with an excitation light and caused the fluorescence of the incorporated nucleotides to light up, which are observed using a CCD camera. Each kind of bases is labeled with a different colored fluorescent dye and the DNA sequence can be determined real time by image processing which identifies the colors. The enzyme immobilization method has an advantage that the position of the bright spots does not blur even in a case of long read since the intake for the enzyme, that is, the fluorescence-labeled bases, is immobilized on the bonding pad 202. With no blurred position, the signals between the adjacent bonding pads are prevented from being intermixed and hence the bonding pads can be arrayed in a higher density manner, thereby increasing the number of parallels. Further, unlike the method in which the template of nucleic acid is immobilized as in Example 1, when the enzyme once immobilized is deactivated, the sequence reaction is not carried out at that reaction site. However, by using in combination with a removable alkyl glucoside linker, the enzyme-attached microparticle can be exchanged together with the linker and the all the enzymes can be refreshed every sequence reaction cycle.

EXAMPLE 3

Figure 3:
FIG. 3 is a drawing showing the steps (a to f) for producing a nucleic acid analysis device of Example 3.
Figure 3:
Figure 3:
Figure 3:
Figure 3:
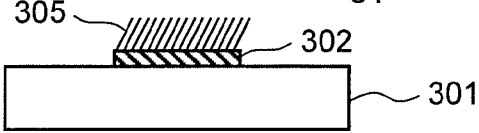
Figure 3:
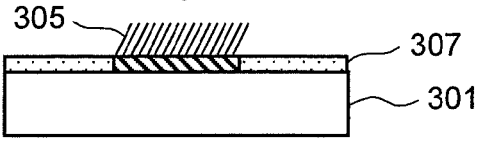

An example of the method for producing a nucleic acid analysis device is described with reference to FIG. 3. A film is produced by sputtering a material composing the bonding pad, e.g., gold, titanium, nickel or aluminum, on a flat support substrate 301 (FIG. 3a) (FIG. 3b). The film produced is to be a metallic thin film (metal deposition film) 308. When a quartz glass substrate or a sapphire substrate is used as the flat support substrate 301 and gold, aluminum or nickel is used as the material for the bonding pad, it is preferable to form a titanium or chromium thin film to reinforce the bonding between the substrate material and the bonding pad material. Additionally, the bonding pad as thin as possible is more preferable. This is because when the flat support substrate 301 is thick, the area on the side portion increases, and even when the diameter of microparticle is less than or equal to the diameter of the bonding pad, a plurality of microparticles may increasingly be likely to be immobilized. For this reason, the metallic thin film 308 is preferably produced as thin as possible at the time of film forming. A pattern is formed using a resist 309 on the metallic thin film 308 (FIG. 3c). Next, the metallic thin film 308 other than the resist pattern is removed by etching (FIG. 3d). The resist 309 is further removed to complete the bonding pad 302. After peeling off the resist, linear molecules 305 selectively adsorbed only by the bonding pad 302 are incorporated (FIG. 3e) to further form a non-specific adsorption prevention film 307 (FIG. 3f).

EXAMPLE 4

Figure 4:
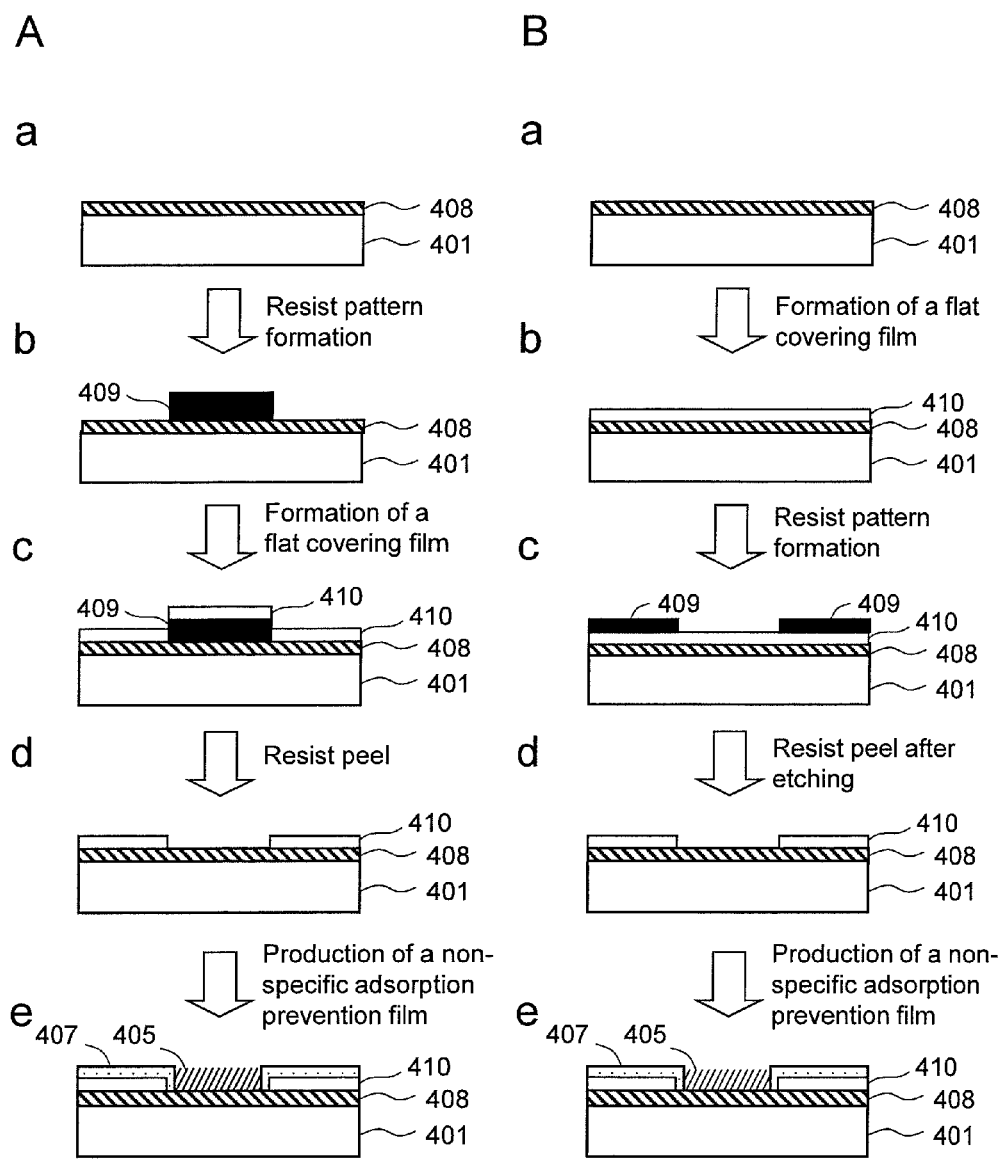
FIGS. 4A and 4B are drawings showing the steps for producing a nucleic acid analysis device of Example 4.

An example of the method for producing a nucleic acid analysis device is described with reference to FIG. 4. An example is shown in which the same materials are used as in Example 3, provided that, for example, a flat covering film 410 composed of a material such as glass is formed on a metallic thin film (metal deposition film) 408 and the flat covering film 410 is processed to carry out patterning. The film is produced on the flat support substrate 401 using the material which composes the bonding pads. In the case of the present example, the material composing the bonding pad must have visible light transmission properties. For example, titanium or aluminum is sputtered to produce a film. This film is to be the thin film 408 (FIG. 4A a, FIG. 4B a). A glass substrate or a sapphire substrate is used as the flat support substrate 401. Additionally, the bonding thin film layer 408 as thin as possible is more preferable. Further, the bonding thin film layer 408 is preferably annealed at 600° C. or more. This is to enhance the transmission rate of the excitation light which irradiates from the bottom side of the substrate. For this reason, the metallic thin film 408 is preferably produced as thin as possible at the time of film forming and annealed.

In FIG. 4A, a pattern is formed on this metallic thin film 408 using a resist 409 (FIG. 4A b). The flat covering film 410 is formed thereon (FIG. 4A c). The resist pattern is removed by etching together with the flat covering film 410 on the resist 409 to complete the patterning of the metal and the flat covering film 410 (FIG. 4A d). In this instance, the region on which the flat covering film 410 does not sit on the metallic thin film 408 of FIG. 4A d serves as the bonding pad. Further, linear molecules 405 are adsorbed to the bonding pad portion and a non-specific adsorption prevention film 407 is further formed on the flat covering film 410 (FIG. 4A e).

In FIG. 4B, the flat covering film 410 is formed on the bonding thin film layer 408 (FIG. 4B b). The pattern of bonding pads is formed thereon using the resist 409 (FIG. 4B c). At this time, by using a positive resist, only the resist of the portion irradiated in the bonding pad patter is removed by etching, and the portion is etched to the outermost surface of the metal. Finally, the remained resist 409 of the resist pattern is removed by etching to complete the patterning of the flat covering film 410 and the metal (FIG. 4B d). In this instance, the region on which the flat covering film 410 does not sit on the metallic thin film 408 of FIG. 4B d serves as the bonding pad. Further, linear molecules 405 are adsorbed to the bonding pad portion and a non-specific adsorption prevention film 407 is further formed on the flat covering film 410 (FIG. 4B e).

EXAMPLE 5

Figure 5:
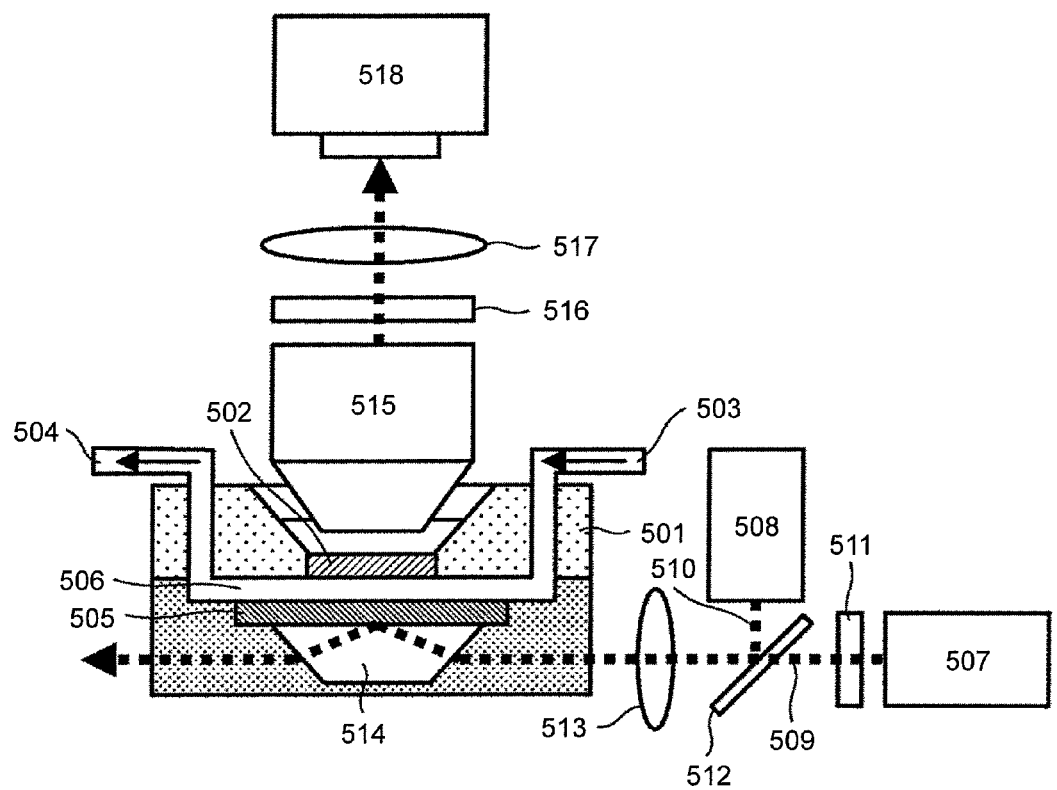
FIG. 5 is a drawing showing the structure of a nucleic acid analyzer of Example 5.

In the present example, an example of the preferable structure for a nucleic acid analyzer which uses the nucleic acid analysis device is described with reference to FIG. 5. The nucleic acid analyzer of the present example comprises at least the nucleic acid analysis device, a means for supplying nucleotides having a fluorescent dye, a nucleic acid polymerase, and a nucleic acid sample to the nucleic acid analysis device, a means for irradiating the nucleic acid analysis device with light, and a luminescence detector for measuring the fluorescence of a fluorescent dye incorporated into a nucleic acid chain through the nucleic acid elongation reaction induced by the coexistence of the nucleotide, the nucleic acid polymerase, and the nucleic acid sample on the nucleic acid analysis device.

More specifically, the above nucleic acid analysis device 505 is set in a reaction chamber consisting of a cover plate 501, a detection window 502, and an inlet 503 and an outlet 504, which are openings for exchanging the solution. PDMS (Polydimethyl siloxane) is used as the material for the cover plate 501 and the detection window 502. Further, the detection window 502 has a thickness of 0.17 mm. Of the laser lights 509 and 510 oscillated from YAG laser light source 507 (wavelength 532 nm, output 20 mW) and YAG laser light source 508 (wavelength 355 nm, output 20 mW), only the laser light 509 is circular polarized using a lambda/4 plate 511 and the above two laser lights are adjusted so as to be on the same axis using a dichroic mirror 512 (reflects 410 nm or less) and condensed with a lens 513 and irradiate the device 505 at a critical angle or more via a prism 514. The fluorescent dyes in the nucleic acid chain are excited with the laser light, and a part of the fluorescence is emitted via the detection window 502. The fluorescence emitted from the detection window 502 is converted to a parallel luminous flux by an objective lens 515 (×60, NA 1.35, working distance 0.15 mm), and the background light and excitation light are blocked off by an optical filter 516, whereby the luminous flux is imaged on a two-dimensional CCD camera 518 by an image forming lens 517. The nucleic acid analysis device is caused to move, and the same measurement can be repeatedly carried out targeting the nucleic acid immobilized on the microparticle on each of the bonding pads.

In the case of the sequential reaction system, a usable nucleotide is that in which 3'-O-allyl group is introduced as a protective group at 3'OH position of the ribose and a fluorescent dye is bound via an allyl group to the 5th position of pyrimidine or the 7th position of purine. Since the allyl group is cut when contact the light irradiation or palladium, both the quenching of dyes and the control of elongation reaction can be achieved at the same times. The unreacted nucleotides do not need to be removed by washing even in the sequential reaction. Further, the real time measurement of the elongation reaction is viable since the washing step is not required. In this case, there is no need to introduce the 3'-O-allyl group as a protective group at 3'OH position of the ribose in the above nucleotide, and the nucleotide, which is bound to a dye via a functional group cuttable by the light irradiation, may be used.

In the case where a semiconductor microparticle is used as the energy transfer medium to the fluorescent dye, the above example of the nucleic acid analyzer is applicable. For example, when Qdot (registered trademark) 565 StreptAvidin conjugated (Invitrogen) is used as the semiconductor microparticle, the YAG laser light source 507 (wavelength 532 nm, output 20 mW) can cause a sufficient excitation. This excitation energy emits fluorescence when transferred to Alexa 633 (Invitrogen), which is not excited by light of 532 nm. In other words, the dyes attached to the unreacted nucleotides are not excited but light up for the first time when captured by the DNA probe and come close to the semiconductor microparticle where the energy transfer occurs, and hence the captured nucleotide can be identified by the fluorescence measurement. When the material of the microparticle for immobilizing the probe molecule is an organic polymer, the excitation is not caused by the light irradiation using an exterior light source. Accordingly, the fluorescent dyes do not light up by the transfer of the excitation energy, and also the unreacted nucleotides light up, likely causing noises. However, when the microparticle such as semiconductor microparticle which causes the energy transfer, is bound to a nucleic acid polymerase, only the incorporated nucleotides are caused to light up. Alternatively, when gold, silver, platinum, aluminum, or the like, is bound to a nucleic acid polymerase, the fluorescence of the incorporated nucleotides can be enhanced. Alternatively, when gold, silver, platinum, aluminum, or the like is used as the material of the bonding pad for immobilizing the microparticle, the fluorescence around the bonding pad is enhanced, thereby increasing the S/N ratio.

In the nucleic acid analyzer of the present invention, an evanescent field is used as the means for irradiating the nucleic acid device with light. More specifically, the evanescent light is irradiated from the means for irradiating light, that is, a laser light oscillated from a laser light source irradiates the device 505 via the prism 514 at a critical angle or more. The fluorescent dye in the nucleic acid chain is excited by the laser light, and a part of the fluorescence stays unreflected but is emitted in the form of evanescent light via the detection window 502 and measured by a fluorescence microscope.

As described above, by assembling a nucleic acid analyzer using the nucleic acid analysis device of the present example, the washing step is obviated, the time required for analysis is cut short, the device and analyzer can be simplified, and the real time nucleotide elongation reaction can also be measured in addition to the sequential reaction system, whereby a significant amount of time is saved in comparison with the conventional art.

The nucleic acid analyzer comprising the nucleic acid analysis device of the present invention can carry out a wide variety of nucleic acid analyses such as determining a DNA sequence and performing hybridization. Particularly, the DNA sequence can be determined (DNA sequence) using the nucleic acid analyzer of the present invention. The method for carrying out the DNA sequence is not limited and is achieved by the method which employs the fluorometric detection.

INDUSTRIAL APPLICABILITY

In the nucleic acid analysis using the nucleic acid analysis device, the dephasing never occurs, and hence the read length is extended as well as many kinds of DNA fragments to be analyzed can be quickly immobilized in a large amount and analyzed, thereby achieving an extremely high throughput.

All publications, patents and patent applications cited herein shall be incorporated per se by reference in the specification.

REFERENCE SIGNS LIST 101, 201, 301, 401 Flat support substrate
102, 202, 302, 402 Bonding pad
103, 203 Microparticle
104 Probe molecule
105, 205, 305, 405 Linear molecule
106, 206 End functional group of the linear molecule
107, 207, 307, 407 Non-specific adsorption prevention film
204 Nucleic acid polymerase
208 Template nucleic acid fragment
209 Nucleic acid substrate
308, 408 Metal deposition film
309, 409 Electron beam resist
410 Flat covering film
501 Cover plate
502 Detection window
503 Inlet
504 Outlet
505 Device
506 Flow channel
507, 508 YAG laser light source
509, 510 Laser light
511 lambda/4 plate
512 Dichroic mirror
513 Lens
514 Prism
515 Objective lens
516 Optical filter
517 Image forming lens
518 Two-dimensional CCD camera

The invention claimed is:

1. A nucleic acid analysis device comprising a support substrate and microparticles having a probe molecule capable of capturing a nucleic acid to be detected, wherein each of the microparticles is immobilized separately from each other on the support substrate,
the nucleic acid analysis device comprises hydrophobically-treated bonding pads at positions at which the microparticles are immobilized on the substrate,
wherein the microparticles are immobilized on the bonding pads by a hydrophobic interaction via a linear molecule having an alkyl chain as a hydrophobic moiety, the alkyl chain including any one of alkylphosphate, alkyl sulfonic acid, and alkyl glycoside and having a length of 3 to 20 in terms of carbon number,
wherein the microparticles are microspheres having an average diameter of 10 nm to 1 µm.

2. The nucleic acid analysis device according to claim 1, wherein a single probe molecule is immobilized on a single microparticle.

3. The nucleic acid analysis device according to claim 1, wherein the microparticles are made of a hydrophobic material or have a hydrophobically conjugated surface.

4. The nucleic acid analysis device according to claim 1, wherein the bonding pads are made of a material selected from the group consisting of gold, titanium, nickel and aluminum.

5. The nucleic acid analysis device according to claim 1, wherein the support substrate is made of a material selected from the group consisting of quartz, sapphire and silicon.

6. The nucleic acid analysis device according to claim 1, wherein the probe molecule is a nucleic acid or a nucleic acid polymerase.

7. A nucleic acid analyzer for obtaining nucleotide sequence information of a nucleic acid sample, comprising:
(i) a nucleic acid analysis device wherein microparticles having a probe molecule capable of capturing a nucleic acid to be detected are regularly immobilized by a hydrophobic interaction on hydrophobically treated bonding pads formed regularly separated from each other on a substrate,
(ii) a means for supplying a nucleotide having a fluorescent dye, a nucleic acid polymerase, and a nucleic acid sample to the nucleic acid analysis device,
(iii) a means for irradiating the nucleic acid analysis device with light, and
(iv) a luminescence detector for measuring fluorescence of a fluorescent dye incorporated into a nucleic acid chain through a nucleic acid elongation reaction induced by the coexistence of the nucleotide, the nucleic acid polymerase, and the nucleic acid sample on the nucleic acid analysis device, wherein the microparticles are immobilized onto the bonding pads by the hydrophobic interaction via a linear molecule having an alkyl chain as a hydrophobic moiety, the alkyl chain including any one of alkylphosphate, alkyl sulfonic acid, and alkyl glycoside and having a length of 3 to 20 in terms of carbon number, wherein the microparticles are microspheres having an average diameter of 10 nm to 1 μm.

8. The nucleic acid analyzer according to claim 7, wherein the probe molecule is a nucleic acid or a nucleic acid polymerase.

9. The nucleic acid analyzer according to claim 7, wherein a single probe molecule is immobilized on a single microparticle.

10. The nucleic acid analyzer according to claim 7, wherein the microparticle is made of a hydrophobic material or has a hydrophobically conjugated surface.

11. The nucleic acid analyzer according to claim 7, wherein the bonding pads of the nucleic acid analysis device are made of a material selected from the group consisting of gold, titanium, nickel and aluminum.

12. The nucleic acid analyzer according to claim 7, wherein the support substrate of the nucleic acid analysis device is made of a material selected from the group consisting of quartz, sapphire and silicon.

13. The nucleic acid analyzer according to claim 7, wherein an evanescent field is used as the means for irradiating the analysis device with light.

* * * * *